United States Patent [19]
Outtrup

[11] Patent Number: 4,604,355
[45] Date of Patent: Aug. 5, 1986

[54] MALTOGENIC AMYLASE ENZYME, PREPARATION AND USE THEREOF

[75] Inventor: Helle Outtrup, Syvendehusvej, Denmark

[73] Assignee: Novo Industri A/S, Denmark

[21] Appl. No.: 591,460

[22] Filed: Mar. 20, 1984

[30] Foreign Application Priority Data

Mar. 25, 1983 [DK] Denmark ............................ 1359/83

[51] Int. Cl.[4] ....................... C12P 19/22; C12P 19/16; C12N 9/26; C12R 1/07
[52] U.S. Cl. ........................................ 435/95; 435/98; 435/201; 435/832
[58] Field of Search ............................ 435/95, 201, 98

[56] References Cited

U.S. PATENT DOCUMENTS 3,804,715  4/1974  Sugimoto et al. .............. 435/201 X
4,011,136  3/1977  Napier ............................ 435/201 X

FOREIGN PATENT DOCUMENTS 147996  11/1979  Japan .................................. 435/201
144087  11/1981  Japan .................................. 435/201

Primary Examiner—Lionel M. Shapiro
Attorney, Agent, or Firm—Fidelman, Wolffe & Waldron

[57] ABSTRACT

A novel maltogenic amylase enzyme with improved thermostability is provided. The novel enzyme can be produced by cultivating a newly discovered microorganism Bacillus strain NCIB 11837 belonging to the *Bacillus stearothermophilus* complex.

5 Claims, 3 Drawing Figures

MALTOGENIC AMYLASE ENZYME, PREPARATION AND USE THEREOF

This invention concerns a novel maltogenic amylase and a process for its preparation.

BACKGROUND OF THE INVENTION

β-amylases are maltogenic exo-amylases which hydrolyse α-1,4-glycosidic bonds from the non-reducing ends of amylose, amylopectin, or glycogen to produce the β-form of maltose. The β-form of maltose will isomerase spontaneously in aqueous solutions to a mixture of the α- and β-form.

β-amylases may be used to produce maltose containing syrups of use in the confectionery -, baking -, and brewing industries.

β-amylases have been isolated from various plants and microorganisms (W. M. Fogarty and C. T. Kelly, Progress in Industrial Microbiology, vol. 15, p. 112-115, 1979). The β-amylases known from plants (barley, sweet potato, and soy beans) and from the Bacillus species *B. mycoides, B. megaterium*, and *B. polymyxa* are all enzymes whose activity is inhibited by sulphydryl reagents, such as PCMB (parachloromecuribenzoate) thus indicating that the active site involves an SH-group.

Hitherto only one β-amylase has been described which is not inhibited by PCMB, namely a β-amylase produced by *Bacillus circulans* (U.S. Pat. No. 4,001,136). The *B. circulans* β-amylase is more thermostable than the above-mentioned β-amylases. However, it is rapidly inactivated at and above 65° C.

In a process for the production of maltose wherein starch in an aqueous medium is hydrolyzed by a β-amylase it is, however, advantageous to use a process temperature of about 65°-70° C. to inhibit retrogradation and to avoid microbial infections.

Therefore, the above mentioned *Bacillus circulans* β-amylase is less than well suited for commercial use at about 65°-70° C. because of too rapid deactivation.

In U.S. Pat. No. 3,804,715 is disclosed a heat resistant β-amylase which is extracted from wheat bran as described in British patent No. 1,130,398. The β-amylase is, however, less attractive in a commercial process as compared with an enzyme derived from a bacterial source because the latter can be produced on a large scale at relatively low costs compared to that of a β-amylase of plant origin.

Therefore, there exists a need for an effective microbial maltogenic amylase preparation which is sufficiently thermostable to be employed at 65°-70° C. for extended periods of time to allow hydrolysis of the starch in an economical way.

It is an object of the present invention to furnish a novel microbial maltogenic amylase which apart from not being inactivated by sulphydryl reagents as PCMB has a higher temperature stability than the microbial β-amylases already known.

The present invention is based upon the discovery that a novel extracellular maltogenic enzyme (C599 amylase) having such properties is produced from a newly isolated microorganism belonging to the *Bacillus stearothermophilus* complex.

For better understanding of the invention herein and the description which follows, attention is directed to the attached drawing wherein:

FIG. 1 is a plot of relative activity of the maltogenic enzyme against temperature and FIG. 2 is a plot of relative activity against pH.

SUMMARY OF THE INVENTION

According to its first aspect, the present invention provides a maltogenic amylase enzyme product which comprises a novel thermostable maltogenic amylase having the following characteristics:

(a) it is obtainable by cultivation in a suitable nutrient medium of Bacillus strain C599 NCIB 11837.

(b) it exhibits the enzyme chemical and immunological properties of the maltogenic amylase derived from the Bacillus strain C599, (c) its activity optimum measured at 30 min reaction time in acetate buffer (0.1M) at pH 5.5 is about 60° C., (d) its pH optimum is at 30 min reaction time in the range of 4.5-6 as determined in a MC Ilvaine buffer at about 60° C. and (e) it has a residual activity after 60 minutes at 70° C. in acetate buffer (0.1M) at pH 5.5 of at least 75%.

The maltogenic amylase product may be in solid or liquid form. Solid forms will generally have an activity of 500-25,000 U (as hereinafter defined) per gram.

According to its second aspect, the present invention provides a process for the preparation of the above maltogenic, thermostable amylase enzyme product which process comprises the cultivation of the above mentioned Bacillus strain C599 or variants or mutants thereof productive of this enzyme in a suitable nutrient medium containing carbon and nitrogen sources and inorganic salts, followed by recovery of the maltogenic amylase enzyme product.

Furthermore, by means of DNA recombinant technique such as described in copending application Ser. No. 591,461 filed concurrently herewith the gene coding for the novel thermostable maltogenic amylase has been transferred into another microorganism which produces, under appropriate conditions of cultivation, substantially greater amounts of the maltogenic amylase than are produced by the donor microorganism (C599).

According to a further aspect the present invention provides a process for the production of high purity maltose syrups wherein starch is treated with the novel maltogenic amylase enzyme product in an aqueous medium.

Tests have shown that the novel maltogenic amylase enzyme product is suitable for the production of maltose and high maltose syrups. Such products are of considerable interest by the production of certain confectioneries because of the low hygroscoposity, low viscosity, good heat stability and mild, not too sweet taste of maltose.

The industrial process of producing maltose syrups comprises liquefying starch, then saccharification with a maltose producing enzyme, and optionally with an enzyme cleaving the 1.6- branching points in amylopectin, for instance an α-1.6- amyloglucosidase.

Although the novel enzyme of this invention in many respects reacts like the known β-amylases it differs therefrom in several essentials as will appear in the following detailed description and, consequently, the novel enzyme is characterized as a maltogenic amylase, rather than a β-amylase.

The novel enzyme migrates at SDS-polyacrylamid gelelectrophoresis as a single band indicating a molecular weight of about 70,000 Dalton. The isoelectric point determined by thin layer gelelectrofocusing is 8.5.

C599 amylase hydrolyzes amylopectin, glycogen, and amylose, maltose constituting a substantial part of the reaction products. Glucose is generated in small amounts corresponding to 1–10% of the maltose formed.

From branched polysaccharides, such as amylopectin and glycogen C599 amylase forms limit dextrins, which can be hydrolyzed by glycoamylase.

Sulphydryl reagents, such as para-chlor-meruribenzoate and chelating agents, such as EDTA do not have any influence on the enzyme activity.

C599 maltogenic amylase differs from the known β-amylases in the following respects:

1. It hydrolyzes Schardinger-cyclodextrins quantitatively. Schardinger-β-cyclodextrin is hydrolyzed into maltose+glucose in a molar ratio of 3:1, whereas α-cyclodextrin is hydrolyzed into maltose+glucose in a molar ratio of 10:1. 'HNMR spectral analysis of α-cyclo dextrins incubated with the maltogenic amylase shows the initial formation of α-maltose as the first main product.

2. Maltotriose is quantitatively cleaved into equimolecular amounts of maltose and glucose. 'HNMR spectral analysis of maltotriose incubated with the maltogenic amylase shows that the hydrolysis product is α-maltose+glucose.

3. It is stable in buffer at 70° C., and 4. the limit dextrins of C599 maltogenic amylase do not form coloured complexes with $I_2$-KI-reagens.

Accordingly the maltogenic amylase according to the invention is an exoenzyme which attacks the α-1,4-glycosidic bonds the main hydrolysis product being α-maltose.

The ability of the maltogenic amylase of the present invention to cleave maltotriose present in the known maltose syrups quantitatively into maltose and glucose thereby increasing the maltose yield is noteworthy as lately there has been an increasing interest in high maltose syrups containing more than 80% maltose.

DETAILED DESCRIPTION OF THE INVENTION

Figure 1:
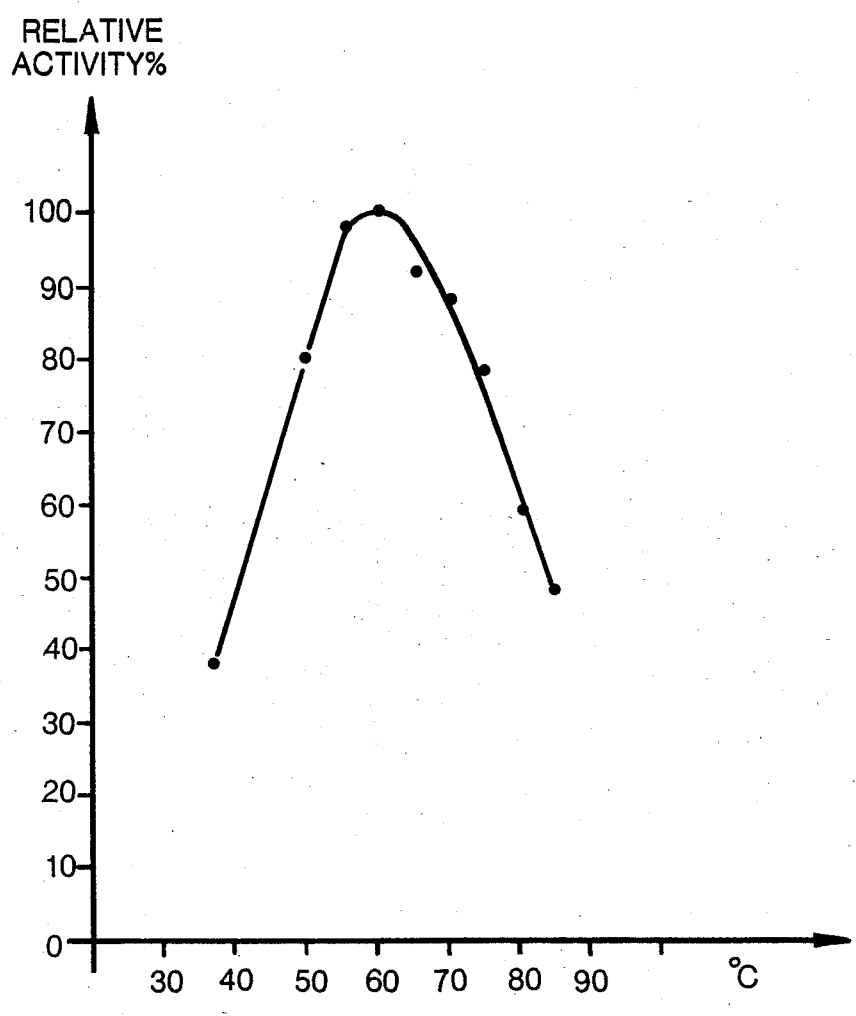

The microorganism capable of producing the maltogenic amylase according to the present invention was selected by means of its ability to grow on an agar substrate prepared as follows:

Tryptone (10 g), amylopectin (CPC snowflake 10 g), Bacto agar (40 g), and deionized water (1000 ml) are mixed aseptically at 55° C. with an equivalent amount of a salt solution of the following composition:

| | |
|---|---|
| $(NH_4)_2SO_4$ | 0.04% by weight |
| $MgSO_4, 7H_2O$ | 0.1% by weight |
| $CaCl_2$ | 0.04% by weight |
| $KH_2PO_4$ | 0.6% by weight | the pH of the salt solution being adjusted to 3.0 with 10N sulphuric acid.

Soil samples collected at Krisuvik, an area with hot springs on Iceland, were spread on the above agar substrate and incubated at 65° C.

After 48 hours the agar surface was coloured with iodine vapour and a colony, C599, surrounded by a zone of uncoloured amylopectin was isolated.

The isolated colony of C599 with underlying agar was incubated over night with starch of pH 4.5 at 60° C. and 70° C. A thin layer chromatography examination revealed maltose as the main product of hydrolysis.

The isolated microorganism C599 was deposited with the National Collection of Industrial Bacteria, Torry Research Station, Aberdeen, Scotland, on Mar. 15, 1983 and accorded the reference number NCIB 11837.

Taxonomy

The recently discovered microorganism according to the present invention is an aerobic rod shaped and spore forming bacterium. Consequently, it belongs to the genus Bacillus.

On agar substrates where the sporulation is poor the culture autolyses rapidly and dies. Therefore, it has been impossible to carry out the taxonomic programme normally used for classification of Bacillus species.

However, the morphology and the temperature for growth which lies between 50° and 70° C. indicates that the new microorganism belongs to the *Bacillus stearothermophilus* complex.

Morphology

The spores are oval, about $1 \times 1.6\mu$ and are terminally to subterminally placed.

The sporangia are strongly swollen and look like rackets or drumsticks.

Determination of Enzyme Activity

One maltogenic amylase unit (U) is defined as the amount of enzyme which under standard conditions (temperature 60° C., pH 5.5, and reaction time 30 minutes) produces reducing sugar corresponding to 1 μmol maltose per minute.

A 0.5% soluble starch (supplied by Merck) in 0.1M acetate buffer or 0.05M phosphate buffer (pH 5) is incubated with 1 ml of the enzyme dissolved in deionized water containing 0.1–0.2 U per ml. The reaction is stopped after 30 minutes by addition of 4 ml 0.5N NaOH.

The content of reducing sugar is then determined by means of the Somogyi method (Somogyi: J.Biol.Chem., 153, p. 375–80 (1944).

An alternative way of determining the enzyme activity is based upon the capability of the maltogenic amylase to quantitatively cleave maltotriose into equimolar amounts of maltose and glucose.

One maltogenic amylase NOVO unit (MANU) is defined as the amount of enzyme which under standard conditions cleaves 1 μmol maltotriose per minute. The enzyme reaction is stopped by shifting pH to about 11. The glucose formed is by means of glucose dehydrogenase (Merck, GlucDH) converted into gluconolactone under formation of NADH. The amount of NADH formed is measured by colorimetric determination at 340 nm.

| Standard conditions: | Temperature 37° C. ± 0.05° C. |
|---|---|
| | pH 5.0 |
| | Incubation time 30 min. |

Reagents 1. 0.1M citrate buffer, pH 5.0

5.255 g citric acid ($C_6H_8O_7$, $H_2O$) is dissolved in about 200 ml demineralized water and pH is adjusted to 5.0 with 4.0/1.0N NaOH. Demineralized water is added up to 250 ml and pH is controlled. The buffer solution may be stored for one week in the refrigerator (pH must be checked before use) but is preferably prepared each test day.

2. Maltotriose substrate 20 mg/ml

To 500 (1000) mg maltotriose (Sigma M 8378) is added citrate buffer (reagent 1) up to 25 (50) ml. To be prepared each test day.

3. GlucDH reagent

Enzyme mixture, Merck No. 14055 flask "1" and "2", is filled up with buffer solution, Merck No. 14051. After 15 min. standing the flask contents are transferred to a 500 ml measuring flask containing about 200 ml buffer (Merck No. 14051) and additional buffer is added up to 500 ml. Stable 14 days in refrigerator.

4. Stopreagent 0.06N NaOH.

Glucose Standard Curve 1.6 g glucose is dissolved in 1000 ml demineralized water and aliquots of 1.0, 2.0, 4.0, 6.0 and 10.0 ml are diluted with demineralized water up to 100 ml. The obtained five standard solutions have a glucose concentration of 88.8, 177.6, 355.2, 532.9 and 888.1 µmol /liter respectively.

The glucose standard curve is made by mixing 2.0 ml of the above glucose standard solutions with 3.0 ml GlucDH reagent and incubating for 30 min. at ambient temperature whereafter $OD_{340}$ is measured. As blank a sample with demineralized water instead of glucose is used.

Enzyme test sample

The test samples are diluted with demineralized water so that the end dilution is within the interval covered by the standard curve.

Assay

To 500 µl enzyme (preheated to 37° C.) was added 500 µl maltotriose substrate (preheated to 37° C.) and the mixture was after careful mixing placed on a water bath (37° C.). After 30 min reaction time the test tube was removed from the water bath and 1000 µl stop reagent was added. 3.0 ml GlucDH reagent was then added and $OD_{340}$ was measured after 30 min standing at ambient temperature.

As blank a sample containing enzyme, stop reagent and maltotriose substrate was used. The maltotriose substrate was not added until immediately after the stop reagent.

Enzyme preparation

A Bacillus strain capable of producing the maltogenic amylase of the present invention is usually propagated on a solid substrate prior to its cultivation under aerobic conditions in a suitable fermentation medium. Both media contain assimilable sources of carbon and nitrogen besides inorganic salts optionally together with growth promoting nutrients, such as yeast extract. The fermentation is typically conducted at 50°–55° C. and at a pH of 6.5 and preferably kept approximately constant by automatic means. The enzyme is excreted into the medium.

The ensuing fermentation broth may be freed of bacterial cells, debris therefrom together with other solids, for example by filtration. The supernatant containing the enzyme may be further clarified, for example by filtration or centrifugation, and then concentrated as required, for example by ultrafiltration or in an evaporator under reduced pressure to give a concentrate which, if desired, may be taken to dryness, for example by lyophilization or spray-drying. Typically, the resulting crude enzyme product exhibits an activity in the range of about 500–25,000 U per gram.

Purification of Enzyme

The maltogenic amylase of the present invention can be purified from a batch fermentation culture broth as follows:

250 liters of culture broth with an enzyme activity of 4 U per ml is filtered and the filtrate is ultrafiltered, germ filtered, and freeze-dried. 193 g of freeze-dried powder are obtained having an activity of 2400 U per g corresponding to 47% of the original activity.

The powder is dissolved in 15 mM acetate buffer, pH 5.0 and dialysed against 15 mM acetate buffer pH 5.0 until the conductivity is about 1 mS. The dialyzate is then applied to a cation exchanger CM-sepharose Cl-6B which has been equilibrated with the same buffer. The amylase passes through the column whereas 60% of the remaining proteins is withheld by the ion-exchanger.

The pH of the effluent from this column is adjusted to 4.0 with acetic acid and the eluate is subsequently applied to a CM-sepharose Cl-6B column equilibrated with 15 mM acetate buffer pH 4.0. Under these circumstances the amylase is adsorbed by the ion-exchanger. The enzyme is then eluated with acetate buffer of pH 4.0 with increasing ionic strength. The enzyme activity in the eluate follows the protein content in a symmetrical peak. The peak material shows a single sharp protein band by SDS-polyacrylamid gel electrophoresis. The MW is about 70,000 Dalton. pI is 8.5 as determined by iso-electric focusing. The specific activity is 325 MANU/mg protein of the crystallized, redissolved and freeze dried product.

Immunological Properties

Monospecific antiserum was generated by immunizing rabbits with purified maltogenic amylase according to the method described by N. H. Axelsen et al., A Manual of Quantitative Immunoelectrophoresis (Oslo 1973) chapter 23.

Crossed immunoelectrophoresis according to the same authors of crude C599 amylase against this serum gave a single peak of immunoprecipitate confirming the monospecificity of the antiserum.

Enzyme Chemical Properties

The dependence of the activity of the maltogenic amylase of this invention on pH and temperature was determined by the method described above using a reaction mixture in which pH and temperature were adjusted to predetermined values.

Reference is again made to the attached drawings in which

Figure 2:
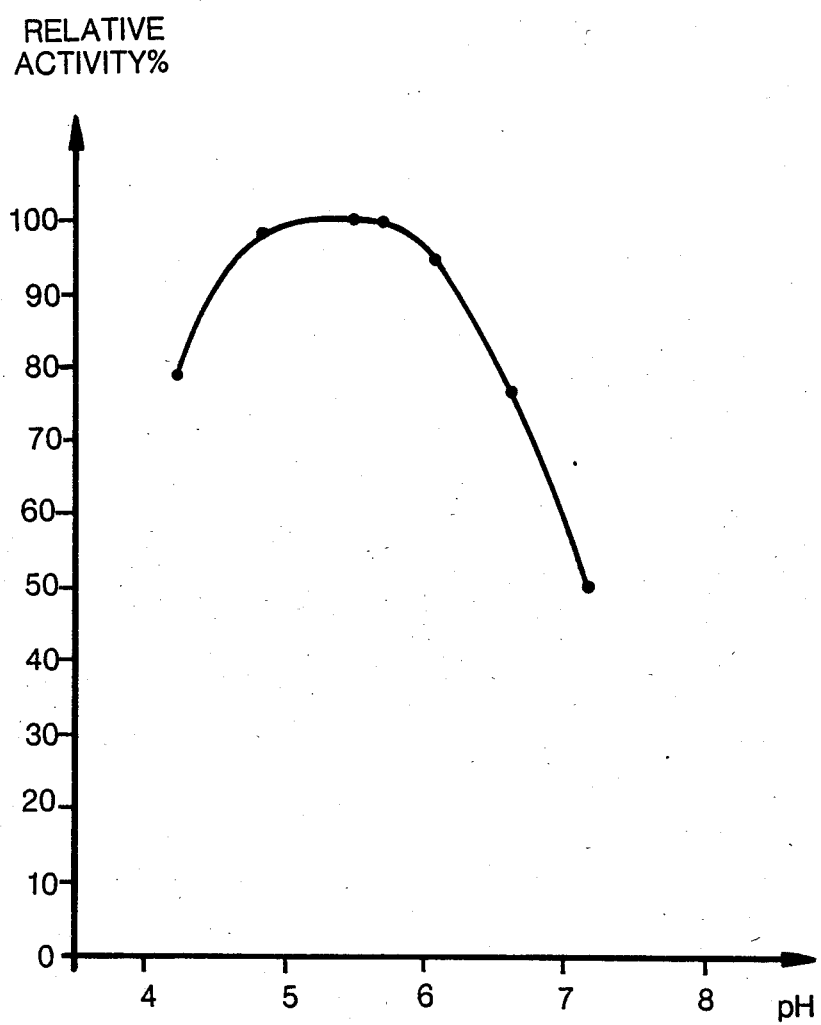
Figure 3:
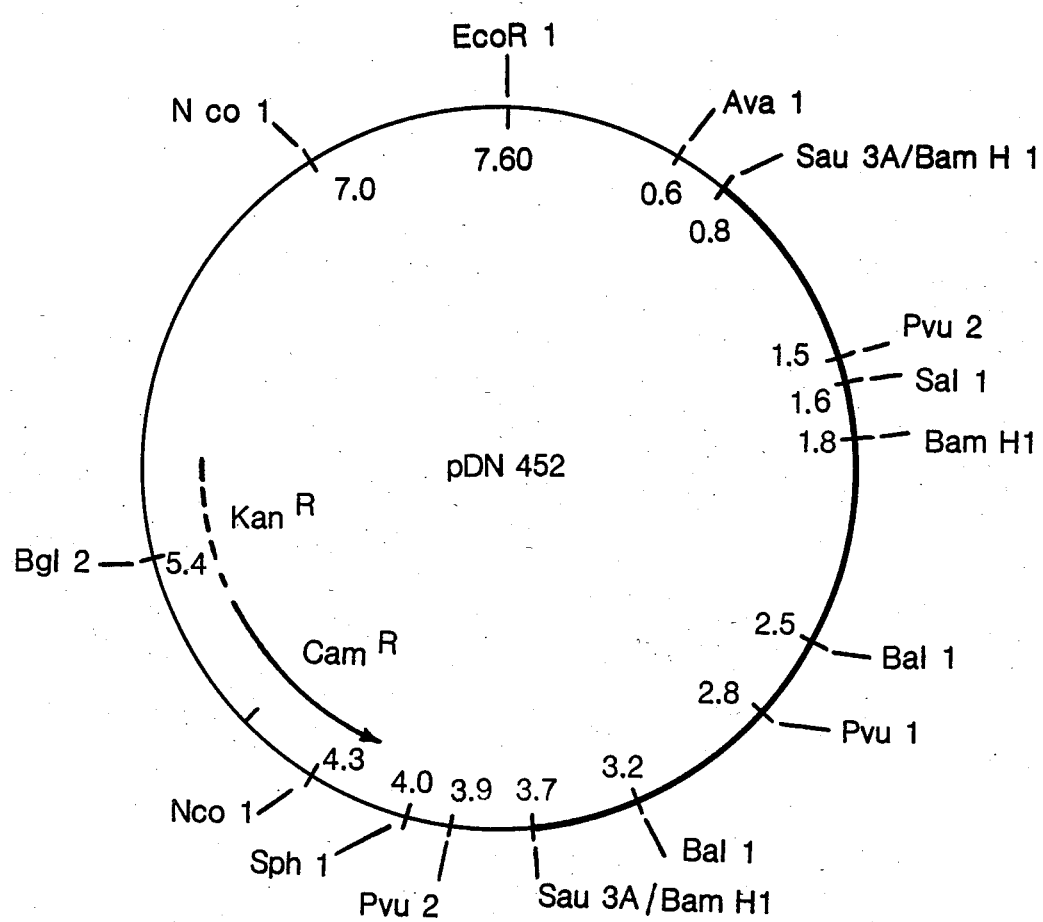

FIG. 1 graphically illustrates the relative activity plotted against temperature (substrate 4% soluble starch, pH 5.5 (0.1M acetate), 30 minutes reaction time) and FIG. 2 graphically illustrates the relative activity plotted against pH (temp. 60° C., substrate 2% soluble starch, 30 minutes reaction time, MC Ilvaine buffer).

It appears from the drawings that C599 maltogenic amylase has an activity optimum at pH 5.5 of about 60°

C. and that its pH optimum is in the range of 4.5–6.0. More than 50% of the maximum activity is still found at 80° C.

In order to determine the thermostability of the maltogenic enzyme the enzyme preparation, 1500 U/g, was mixed with 0.1M acetate buffer (150 mg/ml) of pH 5.5 at a temperature of 50° C., 60° C., and 70° C., respectively. The residual amylase activity was determined by the method described above. The results are presented in the following table:

TABLE I

| Temperature | Time min. | Per cent residual activity |
|---|---|---|
| 50 | 0 | 100 |
|  | 15 | 100 |
|  | 30 | 100 |
|  | 60 | 100 |
| 60 | 0 | 100 |
|  | 15 | 100 |
|  | 30 | 100 |
|  | 60 | 100 |
| 70 | 0 | 100 |
|  | 15 | 90 |
|  | 30 | 80 |
|  | 60 | 75 |

After 60 minutes at 70° C. 75% of the enzyme activity is retained. None of the known β-amylases exhibits such a good thermostability.

The influence of a variety of agents on the activity of the maltogenic amylase of the present invention is shown in the following Table II.

TABLE II

| | Inhibition of C599-amylase | |
|---|---|---|
| Inhibitors | | Residual activity after 60 min. at room temperature, % |
| None | | 100 |
| PCMB, 1 mM | | 92 |
| EDTA, 1 mM | | 104 |
| Schardinger-α-cyclodextrin, 1% | | 109 |
| Schardinger-β-cyclodextrin, 1% | | 107 |
| CaCl$_2$ | 1 mM | 85 |
|  | 10 mM | 73 |
| KCl | 1 mM | 95 |
|  | 10 mM | 94 |
| MgCl$_2$ | 1 mM | 95 |
|  | 10 mM | 93 |
| CoCl$_2$ | 1 mM | 91 |
|  | 10 mM | 44 |
| FeCl$_3$ | 1 mM | 96 |
|  | 10 mM | 74 |
| MnCl$_2$ | 1 mM | 78 |
|  | 10 mM | 52 |
| NaCl | 1 mM | 98 |
|  | 10 mM | 96 |
| CuCl$_2$ | 1 mM | 10 |
|  | 10 mM | 1 |
| ZnCl$_2$ | 1 mM | 51 |
|  | 10 mM | 15 |
| BaCl$_2$ | 1 mM | 98 |
|  | 10 mM | 92 |
| AlCl$_3$ | 1 mM | 98 |
|  | 10 mM | 84 |
| HgCl$_2$ | 0.1 mM | 3 |
|  | 1 mM | 0 |

Ions of heavy metals as $Hg^{++}$ and $Ca^{++}$ inhibit the activity of C599 amylase, whereas neither PCMB, EDTA or Schardinger-cyclodextrins have any effect on the activity.

The following examples are presented as illustrative embodiments of this invention and are not intended as specific limitations thereof.

EXAMPLE 1

Preparation of maltogenic amylase from Bacillus strain C599, deposit number NCIB 11837

The C599 culture was grown at 60° C. for 1–2 days on the following agar:

| Bacto dextrose | 2 g |
|---|---|
| Bacto agar | 25 g |
| Ammonia sulphate | 0.5 g |
| Trace metals + salts as in Bacto Carbon Base (Difco Manual) | |
| Water | 1000 ml |

Inoculum

A freeze-dried culture from the above growth medium was propagated in 500 ml baffled shake flasks in 100 ml of the following substrate:

| Bacto trypton | 10 g |
|---|---|
| Glucose | 10 g |
| Potassium hydrogen phosphate | 3 g |
| Water | 1000 ml |

Incubation was performed for 1–2 days at 50°–55° C.

(a) Batch Fermentation 500 ml shake flasks were charged with 100 ml of a substrate having the following composition:

| NZ-case (Sheffield) | 10 g |
|---|---|
| Yeast extract (Bacto) | 5 g |
| Potassium hydrogen phosphate | 3 g |
| Maltodextrin | 10 g |
| Water | 1000 ml |

The shake flasks were inoculated with 1–5 ml of the above inoculum. Incubation was performed at 50° C. for 2–3 days.

The resulting fermentation broth contained about 10–20 U per ml.

Upscaling from shake flasks to 550 liter steel fermentator can be conducted in a stepwise fashion by increasing the volume of the culture medium by a factor from 3 to 5 in each step.

In 550 liter scale the yield was about 5 U per ml.

(b) Continuous Fermentation

Continuous fermentation was carried out with TMP and SMP substrates having the following composition:

| TMP-substrate: | Trypton (Bacto) | 30 g |
|---|---|---|
|  | Maltodextrin (MCO3L) | 20 g |
|  | Potassium hydrogen phosphate | 3 g |
|  | Pluronic | 0.5 g |
|  | Water | 1000 ml |
| SMP-substrate: | Soy tone (Difco) | 20 g |
|  | Maltodextrin | 10 g |
|  | Potassium hydrogen phosphate | 3 g |
|  | Pluronic | 0.5 g |
|  | Water | 1000 ml |

The fermentation was carried out in an Eschweiler fermentor, type S 10 with 1 liter working volume.

The fermentation was started up with 100 ml of the above inoculum and the substrate dosage was started after 24 hours at 55° C.

The pH was adjusted to 6.5 with 3% sulphuric acid and the temperature was kept at 55° C.

Aerating: 1 liter/liter substrate/minute
Stirring: 1000 rpm
Dilution rate: D=0.05 hr Under the above mentioned conditions the activity yield was 50–75 U per ml on TMP and 40–50 U per ml on SMP.

The Bacillus C599 is a poor producer of the maltogenic enzyme, and therefore, production of the maltogenic enzyme by cultivation of Bacillus C599 would result in a high cost enzyme. A better mode for producing the maltogenic enzyme is through cultivation of a transformed microorganism such as for example the transformed *Bacillus subtilis* strain described by copending application Ser. No. 591,461 filed concurrently herewith.

EXAMPLE 2

Substrates for saccharificaton were prepared by redissolving a 7DE spray-dried maltodextrin in deionized water and making up to approximately 30% D.S. The saccharification experiments were carried out in standard 500 ml laboratory batch reactors. Aliquots of this substrates were heated to 60° C. and the pH adjusted to 5.5 and β-amylase corresponding to Example 1 but produced by cultivation of the appropriately transformed *B. subtilis* as described in copending application Ser. No. 591,461 filed concurrently herewith in amounts of 50 amylase units/g D.S. were then added. After 72 hours at 60° C. the content of glucose, maltose and maltotriose in the syrup was as follows:

glucose: 5%
maltose: 67%
maltotriose: 0%

Saccharification with 25 β-amylase unit/g D.S. Biozym MII (soy bean β-amylase, 20.000 β-amylase/g) under the same conditions gives a syrup containing 0.3% glucose, 61% maltose and 7% maltotriose.

I claim:

1. A maltogenic amylase enzyme obtained by cultivation in a suitable nutrient medium of Bacillus strain NCIB 11837.

2. The maltogenic amylase enzyme product according to claim 1 in solid form exhibiting an amylase activity in the range of from 500 to 25,000 U per gram.

3. A process for the preparation of a maltogenic amylase enzyme wherein Bacillus NCIB 11837 or a variant or mutant thereof is cultivated in a suitable nutrient medium containing carbon and nitrogen sources and inorganic salts followed by recovery of the maltogenic amylase enzyme from the culture broth.

4. A process for producing high purity maltose syrup comprising treating starch in an aqueous medium with the maltogenic amylase enzyme obtained by cultivation in a suitable nutrient meidum of Bacillus strain NCIB 11837.

5. A process for producing high purity maltose syrup according to claim 4 further comprising conducting said process in the presence of an alpha-1,6-glucosidase.

* * * * *